United States Patent
Hart et al.

(10) Patent No.: US 6,558,350 B1
(45) Date of Patent: May 6, 2003

(54) DRAINAGE CATHETER

(75) Inventors: Charles C. Hart, Huntington Beach, CA (US); Ralph V. Clayman, Clayton, MO (US); Said Hilal, Coto de Caza, CA (US); Nabil Hilal, Laguna Niguel, CA (US); John Brustad, Dana Point, CA (US); Bounsavanh Pravongviengkham, Corona, CA (US); Gary R. Dulak, Newport Beach, CA (US)

(73) Assignee: Applied Medical Resources Corp., Rancho Santa Margarita, CA (US)

(*) Notice: Subject to any disclaimer, the term of this patent is extended or adjusted under 35 U.S.C. 154(b) by 227 days.

(21) Appl. No.: 09/598,014

(22) Filed: Jun. 20, 2000

(51) Int. Cl.$^7$ .............................................. A61M 29/00
(52) U.S. Cl. ..................................................... 604/104
(58) Field of Search ................................ 604/104, 105, 604/106, 107, 108, 109, 93.01; 606/191

(56) References Cited

U.S. PATENT DOCUMENTS

| | | | | |
|---|---|---|---|---|
| 3,769,983 A | * | 11/1973 | Merav | 128/207.15 |
| 4,405,314 A | * | 9/1983 | Cope | 128/207.14 |
| 4,407,271 A | * | 10/1983 | Schiff | 600/17 |
| 4,747,823 A | * | 5/1988 | Buchanan | 604/104 |
| 4,893,623 A | * | 1/1990 | Rosenbluth | 604/104 |
| 4,921,484 A | * | 5/1990 | Hillstead | 604/104 |
| 5,147,399 A | * | 9/1992 | Dellon et al. | 606/152 |
| 5,246,445 A | * | 9/1993 | Yachia et al. | 604/104 |
| 5,454,790 A | * | 10/1995 | Dubrul | 604/104 |
| 5,676,688 A | * | 10/1997 | Jaker et al. | 604/104 |
| 5,882,340 A | * | 3/1999 | Yoon | 604/104 |
| 5,957,900 A | * | 9/1999 | Ouchi | 600/104 |
| 5,964,806 A | * | 10/1999 | Cook et al. | 600/30 |
| 6,042,769 A | * | 3/2000 | Gannon et al. | 264/203 |
| 6,210,370 B1 | * | 4/2001 | Chi-Sing et al. | 604/104 |
| 6,344,595 B1 | * | 2/2002 | Phillips et al. | 604/370 |

* cited by examiner

*Primary Examiner*—Teresa Walberg
*Assistant Examiner*—Daniel Robinson
(74) *Attorney, Agent, or Firm*—Richard L. Myers (57) ABSTRACT

A drainage catheter is adapted to drain fluid from the body cavity through a body conduit and includes an elongate tube having a distal end and a retention member disposed at the distal end and adapted for movement between the low-profile state facilitating insertion of the catheter and a high-profile state facilitating the tension of the catheter in its operative position. A woven mesh forms at least a portion of one of the tube and the retention member, and can be made permeable or impermeable in various regions of the catheter. The woven mesh can be formed of filaments heat-settable so that the catheter automatically moves to the high-profile state. Insertion of the catheter can be facilitated using an obturator and a guidewire in an associated method, an obturator facilitating insertion of the catheter can be removed to permit the catheter to automatically return to a normal, high-profile state.

26 Claims, 9 Drawing Sheets

DRAINAGE CATHETER

BACKGROUND OF THE INVENTION

1. Field of the Invention

This invention relates generally to drainage catheters adapted for use in draining a fluid from a body cavity and through a body conduit. Typical of such devices are urinary catheters that are adapted to drain urine from a bladder and through a urethra of a patient.

2. Discussion of the Prior Art

Urinary drainage catheters are used to provide an outlet for the urinary bladder when the normal outlet lumen (the urethra) is compromised or obstructed. Such catheters have been used on a more permanent basis, when the patient is incapable of controlling a capable urinary system due to sedation or lack of mental capacity. A typical urinary catheter is the Foley catheter, which is frequently used for bladder drainage. The Foley catheter is a thick-walled rubber tube with an inflatable balloon near its distal end. The catheter is inserted with the balloon deflated, through the urethra (which extends through the prostate and a bladder neck), and into the bladder cavity. When operably disposed, the balloon is inflated within the bladder cavity to a size that prevents the distal end from passing back through the bladder neck.

There are several disadvantages associated with this catheter and its method of use. Significant among these disadvantages is the construction of the Foley catheter, which typically is manufactured by dip-molding a solid mandrel. Providing the catheter with characteristics for resisting kinking is of particular advantage, but this necessarily requires a significant wall thickness. Foley catheters with a diameter of one-quarter inch or more are typical. This size of catheter is difficult to insert and very uncomfortable for the patient. Patient frustration sometimes leads to inadvisable patient removal, even with the balloon inflated. This of course can be very damaging and traumatic to the patient.

The hard rubber tip of a Foley catheter is also thought to contribute significantly to patient discomfort. As the bladder empties, it collapses and this hard rubber tip begins to rub against the wall of the bladder. The resulting irritation also contributes to patient frustration. Further discomfort results from the fact that the walls of the catheter must be relatively thick and somewhat rigid in order to resist kinking.

Catheters with inflatable balloons must of course provide for an inflation lumen. In a drainage catheter, the primary lumen must be large in order to accommodate the fluid being drained. In order to subtract as little space as possible from this primary lumen, inflation lumens have tended to be relatively small and consequently more susceptible to clogging. Particularly when this clogging results with the balloon inflated, there is no lumen through which the balloon can be deflated. When the Foley catheters of the past had been made from latex, it was possible to respond to a blockage by introducing mineral oil through the primary lumen to attack the latex material of the balloon. This typically results in balloon rupture, enabling the catheter to be withdrawn. Of course, many patients are allergic to latex, so this catheter material cannot be used in all cases.

While the normal flow of urine through the urethra functions as a sterilant, directing the urine through the lumen of the catheter leaves areas between the urethra and the catheter where urine can collect, ultimately resulting in infection. Unfortunately, infections in the urethra transfer rapidly into the bladder. Foley catheters have been provided with anti-bacterial coatings and carefully monitored to avoid infection.

A sphincter at the outward end of the prostate controls the flow of urine from the bladder into the urethra. In some cases, this sphincter is still capable of operation, although a catheter is required to traverse the prostrate. Under these circumstances, the Foley catheter has been undesirable, since its significant wall thickness, although advantageous for kink resistance, inhibits closure by the sphincter.

A Foley catheter is constructed with drainage openings at the distal tip and with the balloon disposed proximally of those openings. With the catheter operatively disposed and the balloon seated against the bladder neck, the openings are positioned well within the bladder cavity. As a result, the bladder does not fully empty, but rather is left with fluid that can be drained only to the level of the openings. This stagnant urine pool is thought to contribute to bladder infection.

SUMMARY OF THE INVENTION

These deficiencies of the prior catheters and methods are overcome with the present invention wherein a drainage catheter is provided with an elongate tube and a retention member, at least one of which is formed of a mesh. This construction enables the catheter to achieve a low insertion profile, and to provide maximum bladder drainage with no residual volume. The catheter has increased flexibility and a high degree of retention with reduced potential for damage if accidentally removed. Normal removal and replacement can be facilitated with the accommodation of a guidewire and obturator.

The retention member can be made from filaments that overlap and define interstices of the mesh. Latex need not be used in the manufacture of the catheter, so the product can be adapted for use even by those allergic to latex. Furthermore, the retention member need not include a balloon requiring an inflation lumen that is susceptible to clogging. Kink resistance is not a problem with the mesh construction, so the wall thickness can be minimal. As a result, the catheter is easily inserted and much more. comfortable for the patient.

Since urine passes outside, inside, and through the mesh, the catheter can facilitate normal urethra function. With the mesh construction, the prostatic sphincter can continue to control the flow of urine to the distal end of the urethra. Foreshortened catheters can also be provided to take advantage of an operable sphincter.

In one aspect of the invention, a drainage catheter is adapted to drain a fluid from a body cavity through a body conduit. The catheter includes an elongate tube having a proximal end and a distal end. A retention member is disposed at the distal end of the elongate tube and adapted for movement between a low-profile state facilitating insertion, and a high-profile state facilitating retention of the catheter in the body cavity. A woven mesh forms at least a portion of at least one of the elongate tube and retention member, the mesh being permeable by the fluid to facilitate drainage of the fluid into the elongate tube of the catheter.

In another aspect of the invention, the drainage catheter includes an elongate tube having a first wall extending between a proximal end and a distal end. A retention member is disposed at the distal end of the elongate tube and has a second wall adapted for movement between a low-profile state facilitating insertion of the catheter and a high-profile state facilitating retention of the catheter. First portions of at least one of the first wall and the second wall are woven and have properties for being permeable to the fluid. Second portions of at least one of the first wall and the second wall are woven and have properties for being impermeable to the fluid.

In a further aspect of the invention, the drainage catheter has an elongate tube and an enlargement member at least one of which has a low-profile state facilitating insertion of the catheter and a high-profile state facilitating operative disposition of the catheter. At least one of the elongate tube and the retention member has properties for automatically expanding from the low-profile state to the high-profile state.

A method associated with a further aspect of the invention relates to a process for inserting a drainage catheter. The catheter is provided with an elongate tube and a retention member at least one of which is formed of woven filaments heat set to a high-profile state. An obturator is placed into the catheter to move the catheter to a low-profile state. The catheter is then inserted and the obturator removed to permit the catheter to automatically return to the heat-set, normal, high-profile state.

These and other features and advantages of the invention will be more apparent with a description of preferred embodiments and reference to the following drawings.

DESCRIPTION OF THE DRAWINGS

FIG. 10 through FIG. 13 illustrate sequential steps in a method for inserting the catheter of the present invention;

DESCRIPTION OF PREFERRED EMBODIMENTS AND BEST MODE OF THE INVENTION

Figure 1:
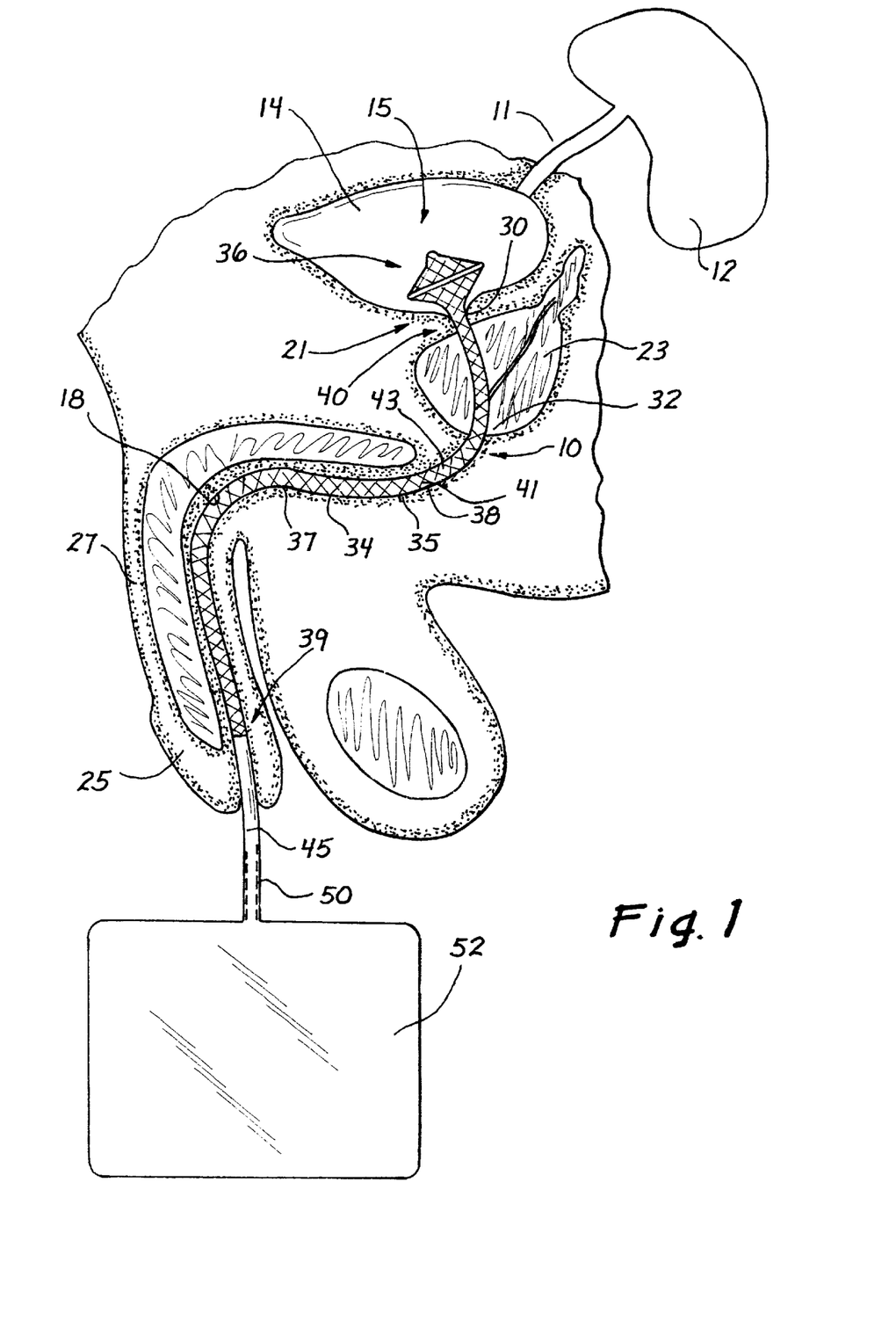
FIG. 1 is a side elevation view of a drainage catheter of the present invention operatively positioned through a urethra and into a bladder cavity of a male patient.

A drainage catheter specifically adapted for use in the urinary tract of a patient is illustrated in FIG. 1 and designated by the reference numeral 10. In this view, the urinary tract includes a ureter 11 extending in fluid communication between a kidney 12 and a bladder 14 having a bladder cavity 15.

A urethra 18 begins at a bladder neck 21 and passes outwardly through a prostrate 23 and a meatus 25 of a penis 27. Sphincters 30 and 32 are disposed at opposite ends of the prostate 23. These sphincters include a secondary sphincter 30 disposed between the prostate 23 and the bladder neck 21, and a primary sphincter 32 disposed at the outward end of the prostate 23. Under normal conditions, the urethra 18 drains urine from the bladder 14 under the control of the sphincters 30 and 32, which open and close the urethra 18.

When the urethra 18 is compromised or otherwise blocked, urine cannot naturally drain from the bladder 14, even when the sphincters 30 and 32 are open. Under these conditions, it becomes desirable to open the urethra 18 or otherwise provide a fluid passage from the bladder 14 through the ureter 18 and the meatus 25.

This is the function of the catheter 10 of the present invention, which includes an elongate tube 34 having a wall 35 which extends distally to a retention member 36. The tube 34 extends along an axis 37 between a proximal end 39 and a distal end 40. In preferred embodiments of the invention, at least portions of the elongate tube 34, and perhaps the retention member 36, are formed of a mesh 38 including filaments 41, which define openings or interstices 43. With the catheter 10 operatively positioned, the urethra 18 is opened, or otherwise augmented with a passage through the tube 34, to drain the urine from the bladder 14. Where the mesh 38 is provided in the retention member 36 or the tube 34, the urine is free to flow through the wall 35, both interiorly and exteriorly of the tube 34. As opposed to the thick-walled catheters of the past, this catheter with the mesh configuration can be easily moved and bent within the urethra 18, even in response to normal movement of the patient. The mesh 38 can be bent and even kinked without affecting the function of the device. Of equal importance is the fact that the wall 35 of the tube 34 can be fully compressed, thereby taking advantage of the natural function of the prostatic sphincter 32.

At the proximal end of the elongate tube 34, a drainage conduit 45 can be connected to the catheter 10 and operatively disposed within the meatus 25, to gather the urine into a drainage lumen 50 which leads to a collection bag 52.

Figure 2:
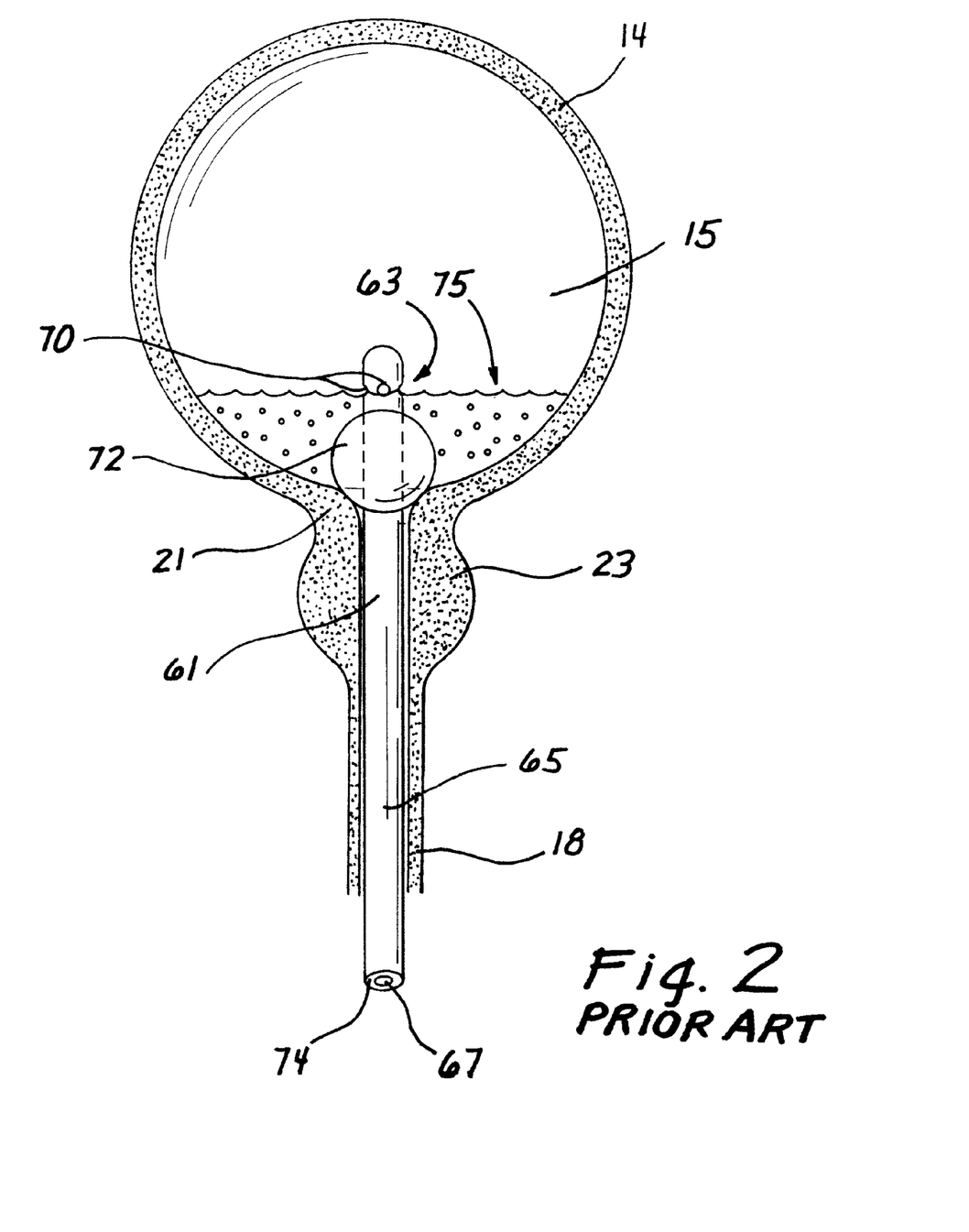
FIG. 2 is a side elevation view partially in section of a prior art Foley catheter operatively disposed in the bladder cavity.

In order to fully appreciate the advantages associated with the catheter 10 of the present invention, a urinary drainage catheter 61 of the prior art is illustrated in FIG. 2. This catheter 61 is a typical Foley catheter operatively disposed to extend through the urethra 18, the prostate 23, and the bladder neck 21, with its distal end 63 positioned in the bladder cavity 15. The Foley catheter 61 includes an elongate shaft 65 having a central drainage lumen 67, and an opening 70 at the distal tip 63 which extend into the drainage lumen 67. A balloon 72 is disposed proximally of the opening 70 and is inflatable through an inflation lumen 74, which extends along the shaft 65.

The walls of the shaft 65 are provided with a considerable thickness in order to add rigidity to the shaft 65. This enhances the kink-resistance and pushability of the Foley catheter 61, unfortunately with commensurate discomfort to the patient. When the Foley catheter 61 is operatively disposed, the balloon 72 is inflated through the lumen 74 so that the distal tip 63 remains in the bladder cavity 15. The balloon 72 tends to seat against the bladder neck 21 so that urine can vacate the bladder cavity 15 only through the opening 70 and the drainage lumen 67. With the opening 70 positioned distally of the balloon 72, the Foley catheter 61 is not capable of fully draining the bladder cavity 15. Rather, a residual volume of urine is maintained between the bladder neck 21 and the opening 70, as illustrated by the arrow 75 in FIG. 2.

As previously noted, the Foley catheter 61 is particularly uncomfortable to the patient, due particularly to its size and inflexibility. Frustrated patients not fully aware of the consequences will sometimes yank the catheter from its operative position, even with the balloon 72 inflated. This is, of course, traumatic and sometimes damaging to the anatomy of the patient. Problems resulting from blockage of the inflation lumen 74 have been previously discussed. As noted, the balloon 72 must also be deflated through this lumen 74, in order to withdraw the Foley catheter 61.

Figure 3A:
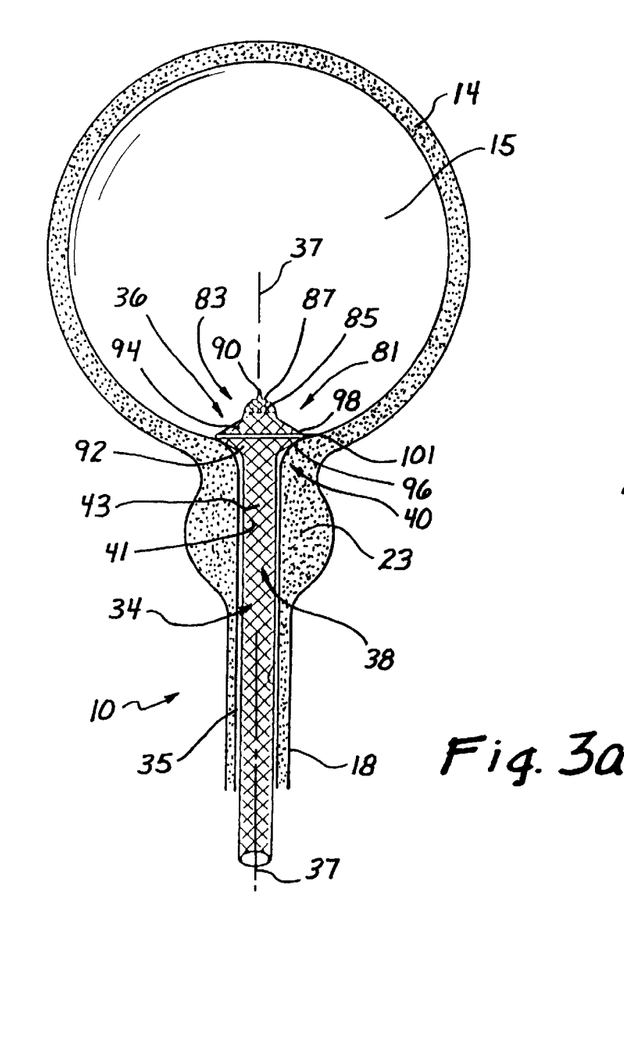
FIG. 3a is a side elevation view partially in section of a preferred embodiment of the present invention operatively disposed in the bladder cavity.

A catheter of the present invention is illustrated in FIG. 3a, operatively disposed to extend through the urethra 18, the prostate 23, and into the cavity 15 of the bladder 14. The elongate tube 34 is shown to be formed from the filaments 41, which define the interstices 43 of the mesh 38. The mesh 38 can be woven or non-woven, preferably into a tubular configuration.

At the distal end 40 of the catheter 10, the retention member 36 can be formed with an enlargement portion 81 and a distal tip 83. Although the retention member 36 could have any of the structures of the prior art, including a balloon, both the enlargement portion 41 and the distal tip 83 of the illustrated embodiment are formed of the mesh, which may be integral with the mesh 38 of the tube 34. At the distal tip 83, the mesh can be provided with additional filaments 85 and smaller interstices 87. A through lumen 90 can be provided in the mesh of the distal tip 83, preferably along the axis 37.

Figure 3B:
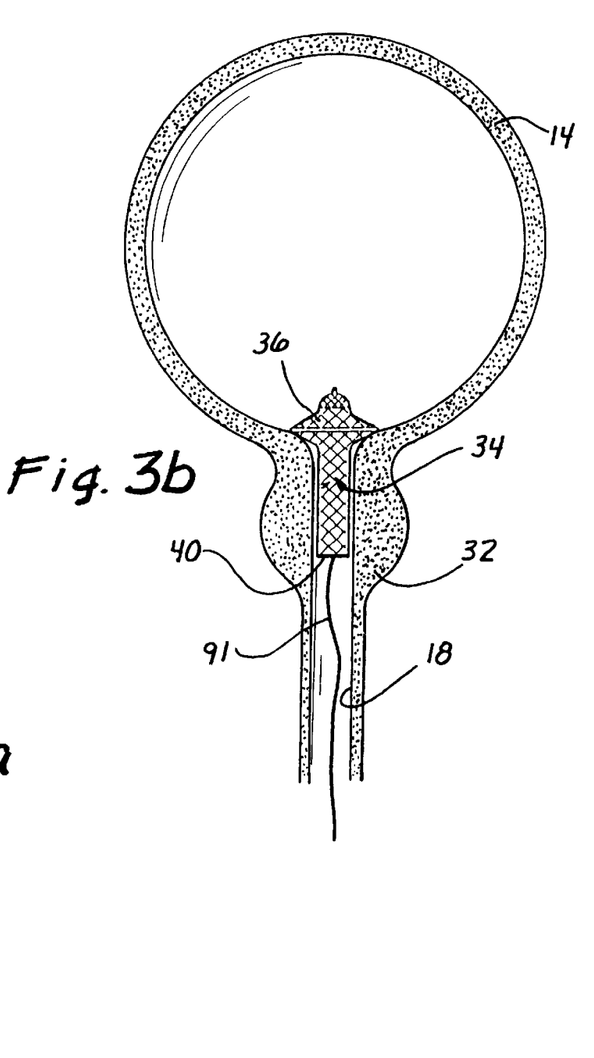
FIG. 3b is a side elevation view similar to FIG. 3a of a foreshortened embodiment of the drainage catheter.

A foreshortened embodiment of the catheter 10 is illustrated in FIG. 3b. In this case, the length of the elongate tube 34 is reduced so that its proximal end 40, when operatively disposed, terminates in the prostate 23 on the bladder-side of the sphincter 32. This construction is particularly appreciated when the sphincter 32 is operative. While the stent 10 facilitates drainage of the bladder 14 into the urethra 18, the sphincter 32 is not required to close against the mesh tube 34 in order to control the flow of urine. A tension device, such as a string 91, can be attached to the proximal end 40 of the elongate tube 32 in order to facilitate removal of the stent 10.

Figure 4:
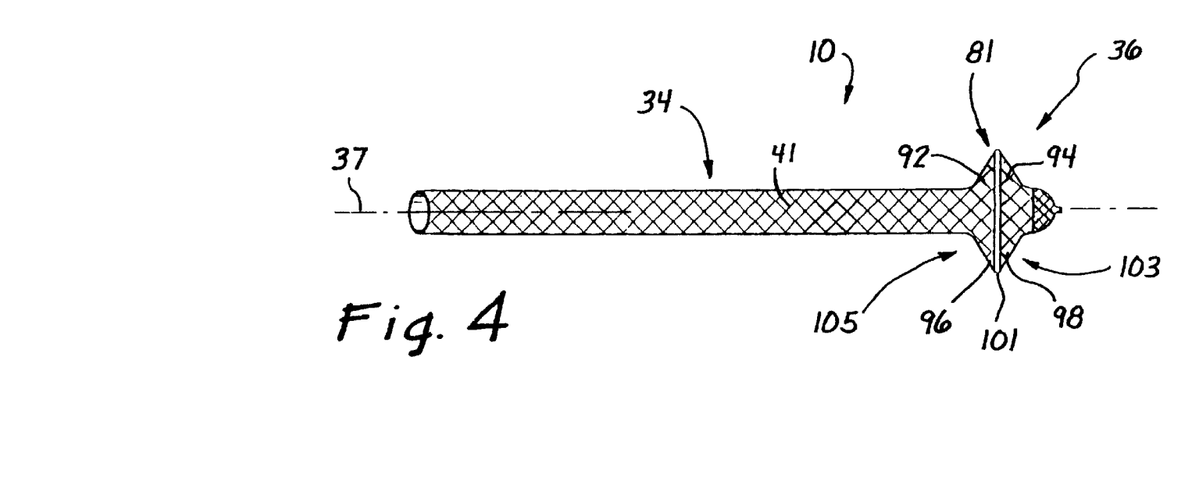
FIG. 4 is a side elevation view of the catheter illustrated in FIG. 3, with the catheter shown in a high-profile state.

The embodiment of FIG. 3a is also illustrated in FIG. 4, which shows in greater detail a preferred construction for the retention member 36. In this construction, the filaments 41 forming the mesh 38 are preferably woven and are movable relative to each other. This characteristic enables the catheter 10 to be stretched between a low-profile state and a high-profile state, discussed in greater detail below. When the filaments 41 are made of polyester or some other heat-settable material, the mesh can be heat set in the high-profile state so that the catheter 10 is automatically biased to a high-profile configuration.

In the high-profile state illustrated in FIG. 4, the enlarged portion 81 of the retention member 36 can be provided with the configuration of two cones 92 and 94 having flared ends 96 and 98, respectively, joined at a circumferential ring 101 and forming sections 105 and 103, respectively. Thus, in the section 105, the proximal cone 92 expands distally to the flared end 96, which terminates at the ring 101. In the section 103, the distal cone 94 faces in the opposite direction, with its flared end 98 extending proximally to the ring 101.

Figure 5:
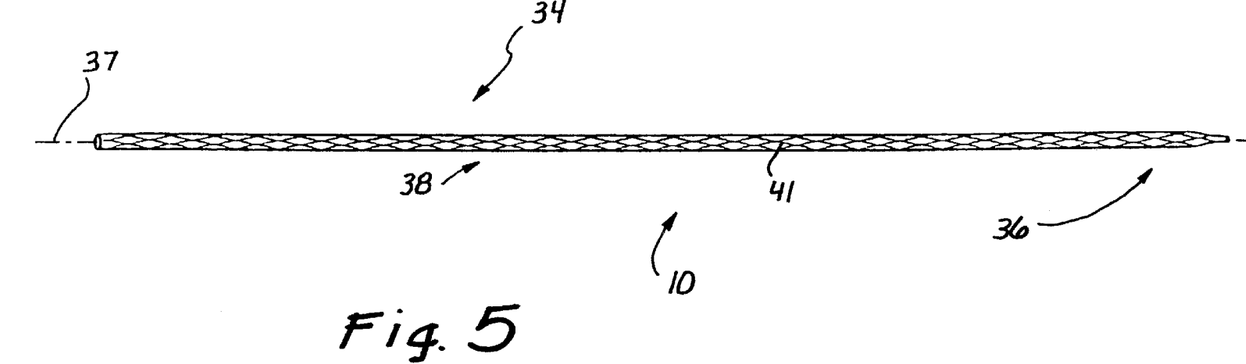
FIG. 5 is a side elevation view of the catheter of FIG. 3, with the catheter shown in a low-profile state.

When the catheter 10 is stretched, the mesh 38 elongates, providing the catheter 10 with a low-profile configuration. In this configuration, the filaments 41 move to a more parallel relationship with the axis 37, as both the elongate tube 34 and the retention member 36 are drawn down to a significantly reduced diameter. This low-profile state is illustrated in FIG. 5 where the catheter 10 is shown to be significantly elongated and much reduced in diameter. This configuration is particularly appreciated when the catheter is inserted and removed from the patient. The construction of the mesh 38 not only facilitates insertion of the catheter 10, but provides a high degree of flexibility, even in a high-profile state, which adds significantly to the comfort of the patient.

Referring again to FIG. 3a, this embodiment of the catheter is shown operatively disposed in the bladder 14. In its high-profile state, the enlarged portion 81 of the retention member 36 is flared outwardly to its high-profile state, where it contacts the bladder neck 21 to retain the distal end 40 of the catheter in the bladder cavity 15. In operation, the urine within the bladder 14 is free to flow through the interstices of the retention member 36, both into and around the elongate tube 34 passing through the urethra 18. With this construction, it is immediately apparent that all of the urine in the bladder 14 is capable of exiting the bladder cavity 15. No residual quantity of urine is left in the bladder 14. As a result, the bladder 14 can be entirely emptied without significant discomfort or risk of infection to the patient.

Figure 6:
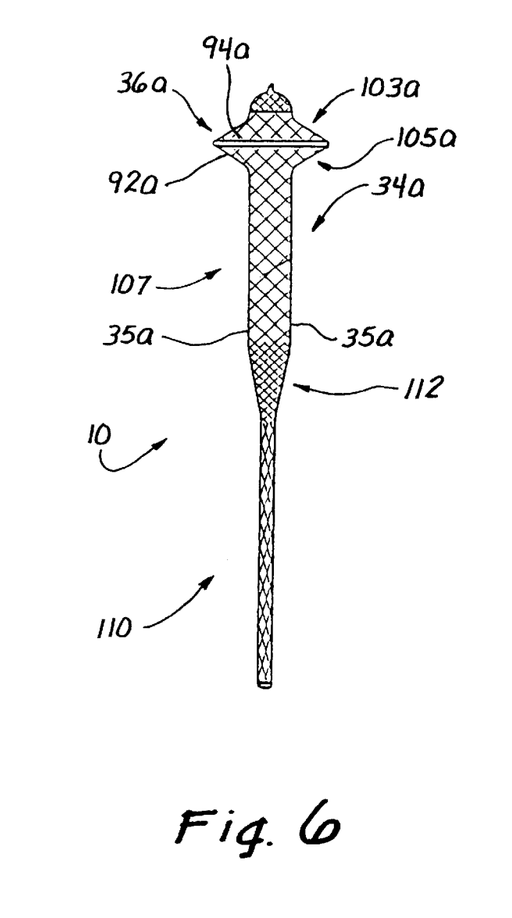
FIG. 6 is a side elevation view of another embodiment of the drainage catheter of the present invention.

Another embodiment of the catheter is illustrated in FIG. 6, where elements similar to those previously discussed are designated by the same reference numeral followed by the lower-case letter "a". For example, the embodiment illustrated in FIG. 6 includes the elongate tube 34a and the mesh retention member 36a. In this case, the elongate tube 34a retains the advantages associated with the embodiment of FIG. 3a. More specifically, the elongate tube 34a has a mesh construction facilitating flow through the wall 35a, so that the urine can continue to function as a sterilizing agent as it flows both inside and outside the elongate tube 34a.

In this embodiment, the retention member 36a is similar to that of the embodiment of FIG. 3, where the two cones 94a and 92a form the first section 103a and second section 105a, respectively, of the retention member 36a. The elongate tube 34a can also be formed in sections, namely a third section 107, a fourth section 110, and a transition section 112. The third section 107 is closely proximate to and perhaps integral with the second section 105a of the retention member 36a. Thus, the third section 107 may be formed from the same mesh as the second section 105a, but with a smaller diameter generally approximating the diameter of the urethra 18.

The diameter of the fourth section 110 may be even further reduced, perhaps to a diameter less than that of the urethra 18. This reduction in diameter is intended to further increase the comfort of the patient when the catheter 10 is operatively disposed.

The transition section 112 will typically have a conical configuration, as it transitions proximally from the larger diameter of the third section 107 to the smaller diameter of the fourth section 110. This transition section 112 can be operably disposed either inwardly of the prostate 23, or outwardly of the prostate 23.

Even though this embodiment of FIG. 6 includes an elongate tube 34a with the three sections 107, 110, and 112, these sections can each be formed of mesh, perhaps with each having a different filament size or weave, in order to incorporate the advantages associated with the mesh construction.

Figure 7:
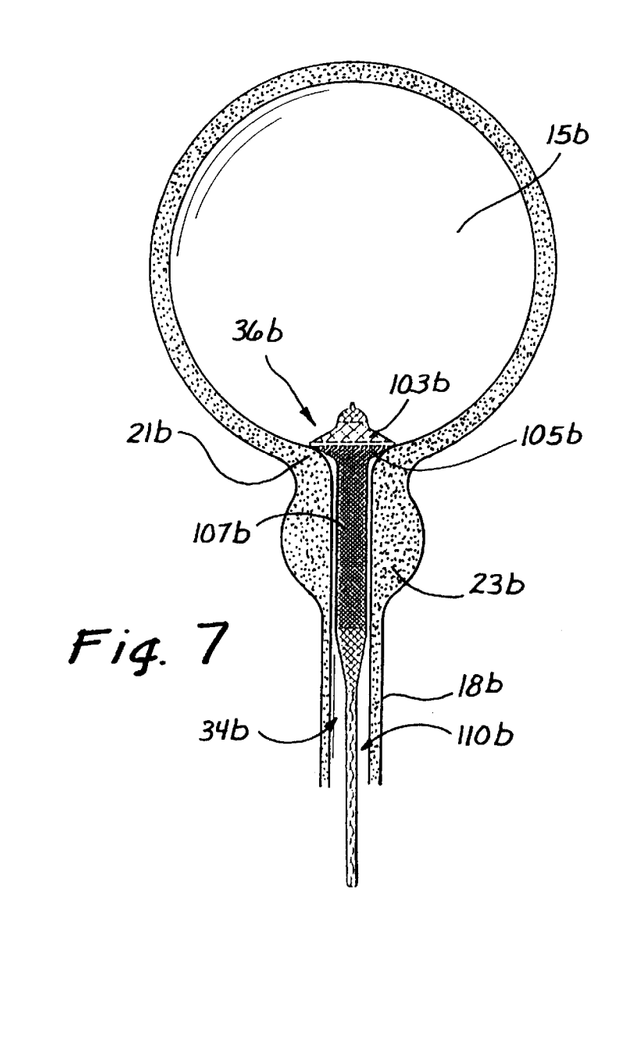
FIG. 7 is a side elevation view of an additional embodiment of the drainage catheter of the present invention.

A further embodiment of the invention is illustrated in FIG. 7, wherein structural elements similar to those previously discussed are designated with the same reference numeral followed by the lower-case letter "b". Thus, this embodiment includes the first and second sections 103b and 105b of the retention member 36b, and also the third and fourth sections 107b and 110b of the elongate tube 34b. The embodiment of FIG. 7 differs from the embodiment of FIG. 6, primarily in the second section 105b and the third section 107b.

While these sections can also be provided with a mesh configuration, the mesh is preferably impregnated, for example with an elastomer, to make it impermeable through this region. This will have at least two effects. With respect to the retention member 36b, an elastomeric coating in the second section 105b will tend to provide the lower section 105b of the retention member 36b with a funnel configuration. Particularly where the coated mesh in this section 105b forms a seal with the bladder neck 21b, the funnel section 105b will operate to gather the urine from the bladder cavity 15b and funnel it into the lumen of the tube 34b. In this embodiment, substantially no urine will flow through the retention member 36b directly into the urethra 18b.

With an impermeable wall in the section 107b, the tube 34b in this region will operate to contain the urine within the lumen of the tube 34b. No urine will flow outwardly of the tube 34b in the section 107b. This feature can be of particular advantage where the urine might interfere with post-operative healing following prostatic surgery. Outwardly of the prostate 23b, the mesh of the tube 34b could be left permeable to take advantage of the sterilizing effect of the urine flowing within the urethra 18b.

Figures 8, 9:
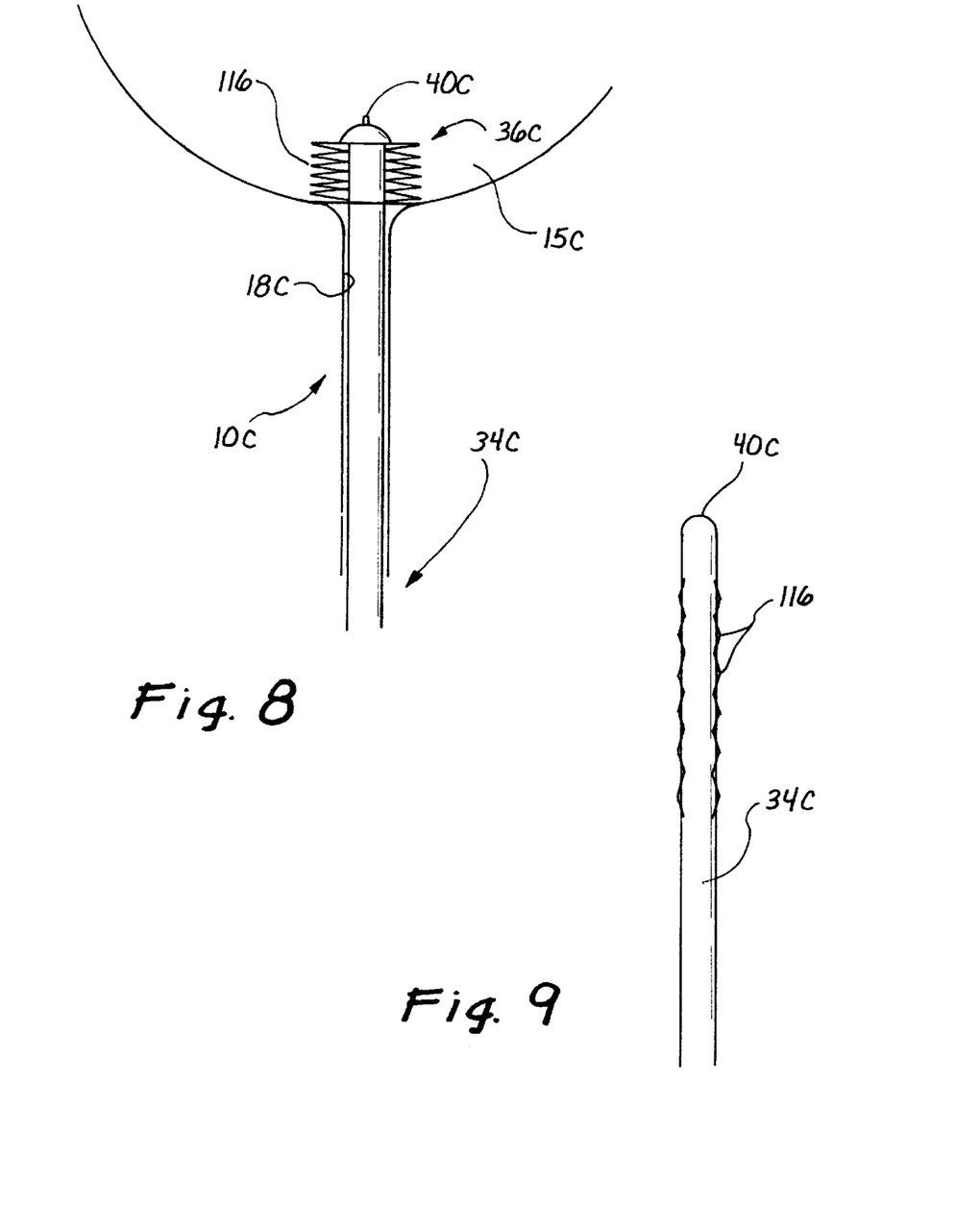
FIG. 8 is a side elevation view of a further embodiment of the drainage catheter of the present invention.
FIG. 9 is a side elevation view showing the catheter of FIG. 8 in a low-profile state.

A further embodiment of the invention is illustrated in FIG. 8, where elements of similar structure are designated with the same reference numeral followed by the lower-case letter "c". In this embodiment, the tube 34c can have any of the constructions previously disclosed; it is the configuration of the retention member 36c that is of particular interest. In this case, the retention member 36c is provided with a single spiral pleat or a plurality of individual annular pleats 116, which are generally stacked axially toward the distal end 40c. The pleats 116, which can also be formed from mesh, will further facilitate movement of the retention member 36c between a contracted high-profile state, as illustrated in FIG. 8, and an expanded low-profile state, as illustrated in FIG. 9. In a preferred embodiment, the filaments forming the mesh of the pleats 116 are heat set to the contracted high-profile state. Thus, a stylet or obturator can be used to insert the catheter 10c in the low-profile state while relying on the intrinsic characteristics of the catheter to automatically return it to the operative, compressed, high-profile state. A further advantage of this pleated construction of the retention member 36c results from the increased hoop strength associated with the pleats 116 in the contracted state. This increased hoop strength of a pleated mesh construction is disclosed in greater detail in applicant's co-pending U.S. patent application, Ser. No. 09/399,211, filed on Sep. 17, 1999, and entitled Mesh Stent with Variable Hoop Strength, which is incorporated herein by reference. Even when the pleats 116 are in the contracted state, urine can flow through the pleats to fully empty the bladder cavity 15c.

Figure 10:
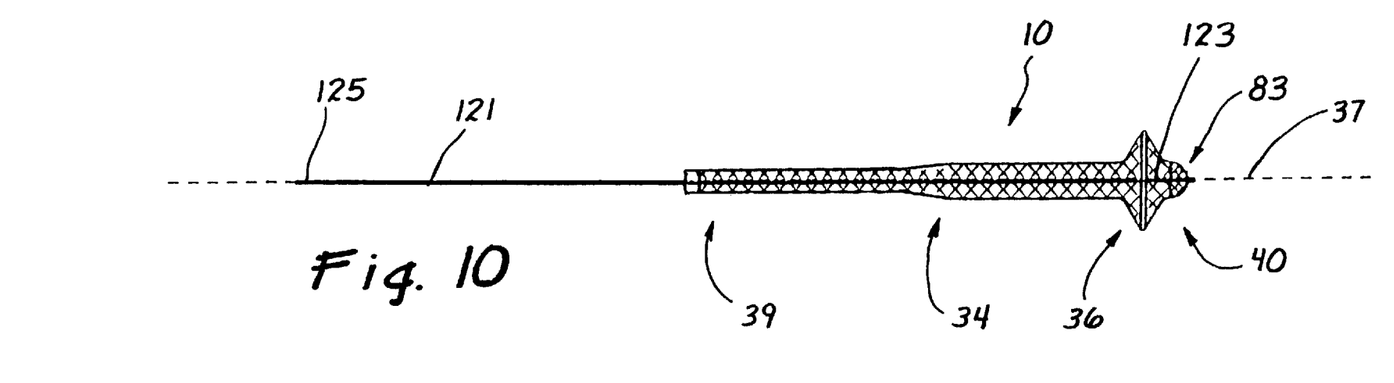
FIG. 10 is a side elevation view of the catheter embodiment of FIG. 7 showing an obturator disposed within the catheter in a high-profile state.
Figure 11:
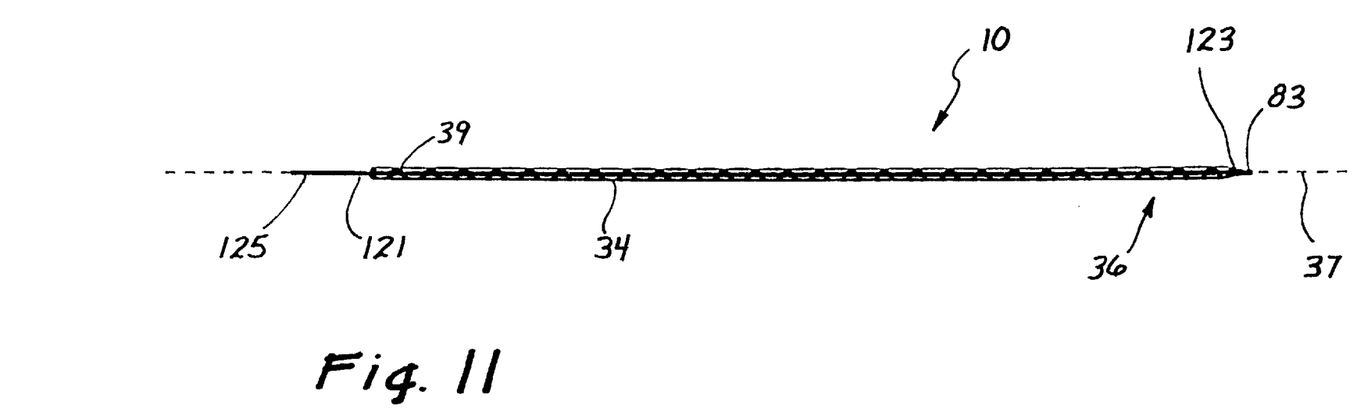
FIG. 11 is a side elevation view showing the catheter longitudinally stretched on the obturator to achieve a low-profile insertion state.

FIGS. 10–13 illustrate a preferred method for moving the catheter 10 to an operative position within the urethra 18 and bladder cavity 15. In FIG. 10, the catheter 10 is illustrated in its normal, relaxed, high-profile state with its proximal end 39 and distal end 40 extending along the axis 37. In this case, the catheter 10 is representative of any of the foregoing embodiments of the invention. In an initial step of insertion, an obturator 121 is provided with a distal end 123 and proximal end 125. The distal end 123 of the obturator 121 can then be inserted into the proximal end 39 of the catheter 10 and moved distally along the elongate tube 34 into the retention member 36 where it contacts the distal tip 83 of the catheter 10. This contact fixes the distal end 123 of the obturator 121 at the distal end 83 of the catheter 10. Grasping the proximal end of the obturator 121 in one hand and the proximal end 39 of the catheter in the other hand, these two ends can be moved toward each other. As the proximal end 125 is advanced toward the proximal end 39, the catheter 10 is drawn down onto the obturator 121, as illustrated in FIG. 11. Where the catheter 10 is formed of mesh, this further movement tends to elongate the catheter 10, but also reduce its diameter. Most notably, the enlarged size of the retention member 36 can be drawn down to substantially the same diameter as the elongate tube 34, which is also reduced in size to about the diameter of the obturator 121. In this insertion step, the catheter 10 is provided with a very narrow, low profile.

Figure 12:
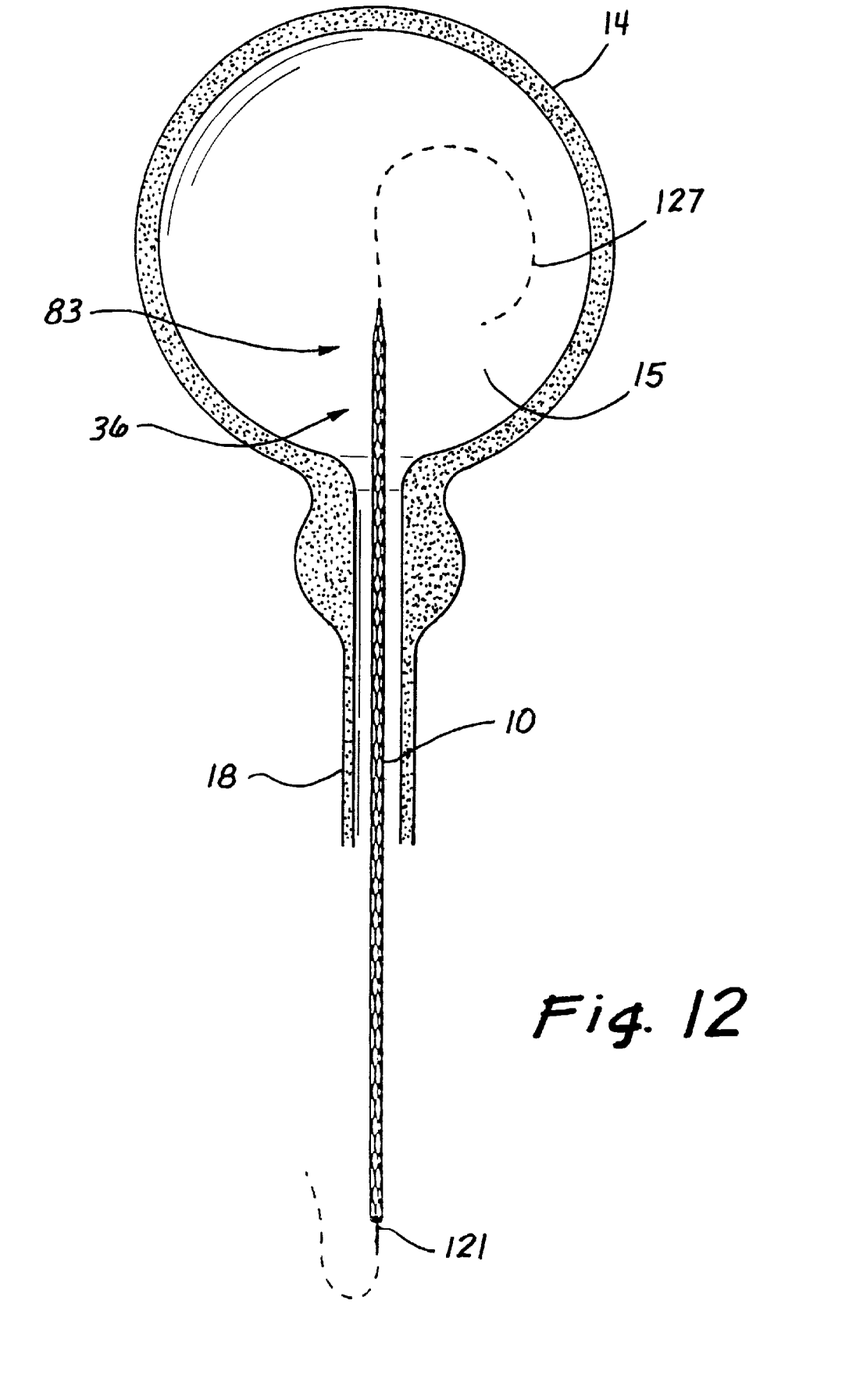
FIG. 12 is a side elevation view showing the catheter inserted over a guidewire, through the urethra, and into the bladder cavity in the low-profile state.
Figure 13:
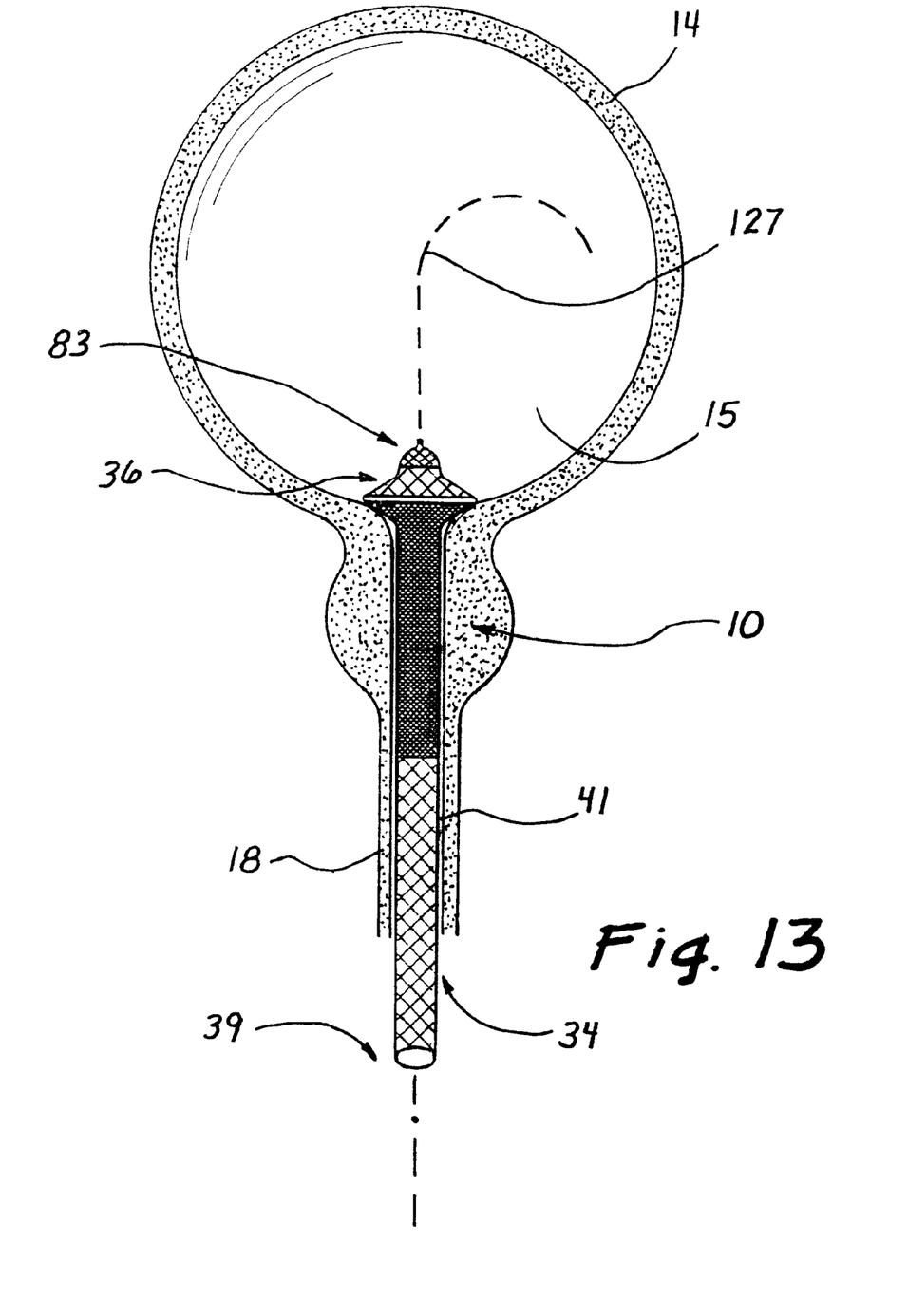
FIG. 13 is a side elevation view of the catheter with the obturator removed and the catheter automatically assuming the high-profile state in its operative position.

Having previously placed a guidewire 127 through the urethra 18 and into the bladder cavity 15, the stretched catheter 10 and the obturator 121 can now be threaded onto the guidewire 127 and moved through the urethra 18 and into the bladder 14. This step of the insertion process is illustrated in FIG. 12. Once the catheter is operatively positioned with its distal tip 83 in the bladder cavity 15, the obturator 121 can be removed, thereby permitting the retention member 36 to expand automatically toward the high-profile state, as illustrated in FIG. 13. This natural axial contraction and radial expansion of the catheter 10 will automatically move the retention member 36 to its enlarged state. Similarly, the filaments 41 of the elongate tube 34 will move generally outwardly into contact with the urethra 18. Alternatively, the proximal end 39 of the catheter 10 can be released from proximity to the proximal end 125 of the obturator 121. This will also enable the catheter 10 to move automatically toward its high-profile state, even if the obturator 121 is left in place.

The foregoing embodiments and methods relate to the concept of a drainage catheter wherein portions of an elongate tube and retention member are formed of a mesh. The mesh forms walls which are typically permeable by the fluid to be drained, so that drainage occurs inside, outside, and through the mesh wall. In a ureteral catheter, flow outside the wall facilitates sterilization and inhibits infection.

Although the mesh retention member has been disclosed to facilitate both drainage and anchoring, it will be apparent that its advantageous drainage characteristics can also be achieved in embodiments where anchoring is accomplished with other structures. For example, the mesh configuration can be advantageously combined with an anchor in the form of a balloon, or a structure wherein an anchor is formed by bending the distal tip of the catheter back on itself. In each of these configurations, the mesh structure will typically be formed distally of the anchor structure in order to facilitate drainage through the catheter.

The mesh can be heat set to bias the catheter from a low-profile configuration to a high-profile configuration.

The low-profile configuration, which can be achieved using an obturator which facilitates insertion of the catheter, for example, over a guidewire. Since the mesh catheter can function when bent or even kinked, it need not be provided with thick walls. As a result, the catheter is considerably more comfortable to the patient.

With the wide variety of features and advantages associated with both the apparatus and method of the present invention, one is cautioned not to restrict the concept merely to the embodiments disclosed, but rather to determine the scope of the invention only with reference to the following claims.

What is claimed is:

1. A drainage catheter adapted to drain a fluid from a body cavity through a body conduit, comprising:
    a single elongate tube having a proximal end and a distal end, and being sized and configured for insertion through the body conduit and into the body cavity;
    an automatically expandable retention member disposed at the distal end of the elongate tube and being adapted for movement between a low-profile state facilitating insertion of the catheter through the body conduit, and an expanded high-profile state facilitating retention of the distal end of the catheter in the body cavity; and
    a plurality of woven filaments forming at least a portion of at least one of the elongate tube and the retention member, the woven filaments being permeable by the fluid to facilitate drainage of the fluid into the elongate tube of the catheter.

2. The drainage catheter recited in claim 1, wherein:
    the woven filaments form at least a portion of the retention member and include permeable interstices through which the fluid can pass from the body cavity into the elongate tube of the catheter.

3. The drainage catheter recited in claim 1, wherein:
    the woven filaments form at least a portion of the elongate tube and have a first normal state with a first diameter and a first length, and a second insertion state with a second diameter less than the first diameter and a second length greater than the first length.

4. The drainage catheter recited in claim 3, further comprising:
    an obturator removably insertable into the elongate tube and operable from the proximal end of the elongate tube to move the woven filaments from the first normal state to the second insertion state.

5. The drainage catheter recited in claim 3, wherein:
    the woven filaments forming at least the portion of the elongate tube are heat set to the first normal state.

6. The drainage catheter recited in claim 1, wherein:
    a distal tip formed on the retention member and defining an opening sized and configured to receive a guidewire for guiding the catheter through the body conduit and into the body cavity.

7. The drainage catheter recited in claim 1, wherein:
    the woven filaments form a mesh.

8. The drainage catheter recited in claim 7, wherein the body cavity and the body conduit are defined by body tissue, and the woven filaments include at least one filament chemically treated to perform a chemical function on at least one of the fluid and the body tissue.

9. A drainage catheter adapted to drain a fluid from a body cavity and through a body conduit, comprising:
    a single elongate tube having a first wall extending between a proximal end and a distal end, the first wall being sized and configured for insertion through the body conduit and into the body cavity;
    an automatically expandable retention member having a second wall and being disposed at the distal end of the elongate tube, the second wall of the retention member being adapted for movement between a low-profile state facilitating insertion of the catheter through the body conduit and an expanded high-profile state facilitating retention of the distal end of the catheter in the body cavity;
    first portions of at least one of the first wall and the second wall being woven and having properties for being permeable to the fluid; and
    second portions of at least one of the first wall and the second wall being woven and having properties for being impermeable to the fluid.

10. The drainage catheter recited in claim 9, wherein:
    the first portions include a first section of the retention member;
    the second portions include a second section of the retention member;
    the second section of the retention member is adapted to form a seal with the body conduit at the body cavity.

11. The drainage catheter recited in claim 9, wherein:
    the first portions include a first section of the elongate tube;
    the second portions include a second section of the elongate tube; and
    the second section of the elongate tube is disposed in juxtaposition to the retention member.

12. The drainage catheter recited in claim 10, wherein:
    the first portions include a third section of the elongate tube;
    the second portions include a fourth section of the elongate tube; and
    the fourth section of the elongate tube is disposed in juxtaposition to the second section of the retention member.

13. The drainage catheter recited in claim 9, wherein:
    the second portions include a first section of the retention member and a second section of the elongate tube; and
    the first section of the retention member is disposed in juxtaposition to the second section of the elongate tube.

14. The drainage catheter recited in claim 11, wherein:
    the first section of the elongate tube has a first diameter;
    the second section of the elongate tube has a second diameter larger than the first diameter.

15. The drainage catheter recited in claim 14, further comprising:
    a transition section disposed between the first section of the elongate tube and the second section of the elongate tube; and
    the transition section having the shape of a frustum of a cone.

16. A method for inserting a drainage catheter through a body conduit and into a body cavity, comprising the steps of:
    providing the drainage catheter with a single elongate tube and an automatically expandable retention member With at least one of the elongate tube and the retention member being formed by woven filaments heat set to an expanded high-profile normal state;
    placing an obturator into the drainage catheter to move the catheter to a low-profile insertion state;

inserting the obturator and the drainage catheter in the low-profile insertion state into the body conduit and the body cavity; and removing the obturator from the drainage cavity to permit the drainage catheter to return automatically to the heat-set, normal, expanded high-profile state.

17. A drainage catheter adapted to drain fluid from a body cavity and through a body conduit, comprising:

a single elongate tube having a proximal end and a distal end, and being sized and configured for operative disposition in the body conduit;

a retention member disposed at the distal end of the elongate tube and being sized and configured for operative disposition in the body cavity;

at least one of the elongate tube and the retention member having a low-profile state facilitating insertion of the catheter and a high-profile state facilitating operative disposition of the catheter; and the one of the elongate tube and the retention member having properties for automatically expanding from the low-profile state to the high-profile state.

18. The drainage catheter recited in claim 17 wherein the one of the elongate tube and the enlargement member is the elongate tube.

19. The drainage catheter recited in claim 17 wherein the one of the elongate tube and the enlargement member is the enlargement member.

20. The drainage catheter recited in claim 18 wherein both the elongate tube and the enlargement member have properties for automatically expanding from the low-profile state to the high-profile state.

21. The drainage catheter recited in claim 17, further comprising:

an obturator operable from the proximal end of the elongate tube to manually move the one of the elongate tube and the enlargement member from the high-profile state to the low-profile state to facilitate insertion of the catheter through the body conduit and into the body cavity.

22. The drainage catheter recited in claim 17, further comprising:

a multiplicity of filaments woven to form the one of the elongate tube and the enlargement member.

23. The drainage catheter recited in claim 22 wherein the multiplicity of filaments have properties for being heat set to the high-profile state.

24. The drainage catheter recited in claim 17 wherein elongate tube has a column strength of substantially zero.

25. A method for placing a urinary catheter in an operative position relative to a bladder, a urethra, and a sphincter of a patient, comprising the steps of:

providing a catheter with a single elongate tube having a proximal end and a distal end, with an automatically expandable retention member disposed at the distal end and being automatically biased from a low-profile state to an expanded high-profile state;

inserting the catheter into the urethra in the low-profile state, to the operative position wherein the retention member is disposed in the bladder; and permitting the retention member to automatically return to the high-profile state within the bladder to retain the catheter in the operative position.

26. The method recited in claim 25 further comprising the steps of:

providing the catheter with a tension member attached to the proximal end of the tube;

during the inserting step, moving the catheter to the operative position wherein the proximal end of the tube is disposed in the urethra between the bladder and the sphincter; and pulling on the retention member to remove the catheter from the operative position.

* * * * *